United States Patent [19]

Lunts et al.

[11] 4,066,755
[45] Jan. 3, 1978

[54] PHENYLAMINOETHANOL DERIVATIVES FOR TREATING HYPERTENSION

[75] Inventors: Lawrence Henry Charles Lunts; David Trevor Collin, both of London, England

[73] Assignee: Allen & Hanburys Limited, London, England

[21] Appl. No.: 753,558

[22] Filed: Dec. 22, 1976

Related U.S. Application Data

[60] Division of Ser. No. 420,547, Nov. 30, 1973, Pat. No. 4,012,444, which is a continuation of Ser. No. 59,979, June 29, 1970, abandoned.

[30] Foreign Application Priority Data

July 8, 1969 United Kingdom .............. 34379/69

[51] Int. Cl.$^2$ ............................................ A61K 31/60
[52] U.S. Cl. .................................................. 424/230
[58] Field of Search ........................................ 424/230

[56] References Cited
PUBLICATIONS

Chem. Abst. 8th Coll. Index, vols. 66–75, (1967–1971), pp. 15505S–15512S.

Primary Examiner—Sam Rosen

Attorney, Agent, or Firm—Bacon & Thomas

[57] ABSTRACT

Compounds of the formula:

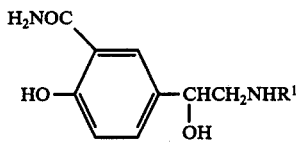

and physiologically acceptable acid addition salts thereof, in which $R^1$ is a. an arylalkyl group, the alkyl portion of which contains from 1 to 6 carbon atoms and the aryl portion of which may be substituted by one or more alkoxy groups or hydroxy groups; or b. an aryloxyalkyl group, the alkyl portion of which contains from 1 to 6 carbon atoms, and the aryloxy portion of which is substituted with one or more alkoxy or hydroxy groups.

These compounds have a blacking action on both α- and β-adrenergic receptors and are useful in treating hypertension. Processes for the production of these compounds and pharmaceutical compositions containing them are also provided.

10 Claims, No Drawings

PHENYLAMINOETHANOL DERIVATIVES FOR TREATING HYPERTENSION

This is a division of application Ser. No. 420,547, filed Nov. 30, 1973, now U.S. Pat. No. 4,012,444, which is in turn a continuation of application Ser. No. 50,979, filed June 29, 1970, and now abandoned.

This invention relates to novel-1-phenyl-2-aminoethanol derivatives having biological activity, and to compositions containing the same, and to processes for preparing such derivatives. It is an improvement of the invention described in application Ser. No. 669,263, of Lunts et al filed Sept. 20th, 1967.

In that application there are disclosed compounds of the formula:

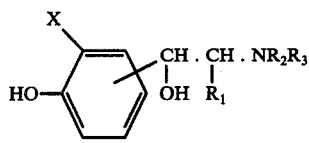

and physiologically acceptable acid addition salts thereof in which:

$R_1$ represents a hydrogen atom or a straight or branched chain alkyl radical containing from 1 to 6 carbon atoms;

$R_2$ represents a hydrogen atom or a benzyl group;

$R_3$ represents a hydrogen atom, or a straight or branched chain alkyl radical containing from 1 to 6 carbon atoms, which radical may be substituted by hydroxyl groups, amino groups or heterocyclic rings, containing one or more heteroatoms, for example morpholino, or represents a cycloalkyl, aralkyl or aryloxyalkyl radical, which radicals may optionally be substituted, for example by one or more alkoxy or hydroxy groups; and X represents a hydroxyalkyl or hydroxyaralkyl radical having a straight or branched alkyl chain containing from 1 to 6 carbon atoms, or a carboxyl radical, or an alkoxy carbonyl radical of the formula —$COOR_4$, (where $R_4$ represents a straight or branched chain alkyl radical containing from 1 to 6 carbon atoms), or represents a radical of the formula —CONHOH or —$CONHNH_2$ or an amido radical of the formula —$CONR_5R_6$ (where $R_5$ and $R_6$, which may be the same or different, each represents a hydrogen atom or an arylalkyl radical or a straight or branched chain alkyl radical containing from 1 to 6 carbon atoms which may be substituted by hydroxyl or amino groups or where $R_5$ and $R_6$ together with the adjacent nitrogen atom form a heterocyclic ring which may contain further heteroatoms).

These compounds possess either stimulant or blocking actions on β-adrenergic receptors.

This invention relates to certain novel-1-phenyl-2-aminoethanols which fall within the general formula I given above but which have been found to have the special and particular utility of blocking both the α- and β-adrenergic receptors. They may be used as hypotensive agents and in the treatment of peripheral disorders, such as Raynaud's disease, with a minimum of side effects. They are also of value in the treatment of angina pectoris.

The invention therefore provides as new compounds, compounds of the formula:

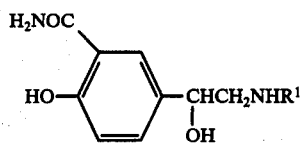

and physiologically acceptable acid addition salts thereof, in which $R^1$ is a. an arylalkyl group, the alkyl portion of which contains from 1 to 6 carbon atoms and the aryl portion of which may be substituted by one or more alkoxy groups or hydroxy groups b. an aryloxyalkyl group, the alkyl portion of which contains from 1 to 6 carbon atoms, and the aryloxy portion of which is substituted with one or more alkoxy or hydroxy groups.

Preferred compounds according to the invention are those in which the alkyl portion of the group (a) or group (b) contains from 3 to 4 carbon atoms; in which, where the aryl portion or aryloxy portion contains an alkoxy substituent, this contains from 1 to 6 carbon atoms, preferably 1 to 4 carbon atoms, and is in particular a methoxy or ethoxy group.

A preferred aryl group is the phenyl group. A preferred aryloxy group is the phenoxy group. More than one aryl or aryloxyl group may be attached to the alkyl group and the definition aralkyl and aryloxyalkyl extends to such possibilities. An example of such a case is 1-methyl-3,3-diphenylpropyl.

Preferred compounds according to the invention are:

5-[1-hydroxy-2-(1-methyl-3-phenylpropyl)aminoethyl]-salicylamide.

5-[1-hydroxy-2-(p-methoxy-α-methylphenethyl)aminoethyl]salicylamide.

5-[1-hydroxy-2-(2-p-methoxyphenoxy-1-methyl-ethyl)aminoethyl]salicylamide.

5-[1-hydroxy-2-(3-p-methoxyphenyl-1-methyl-propyl)aminoethyl]salicylamide.

5-[1-hydroxy-2-(3-phenylpropyl)aminoethyl]salicylamide hydrochloride.

5-[1-hydroxy-2-(2-o-methoxyphenoxy-1-methyl-ethyl)aminoethyl]salicylamide.

5-[1-hydroxy-2-(3-p-hydroxyphenyl-1-methylpropyl)aminoethyl]salicylamide hydrochloride.

5-[1-hydroxy-2-(1-methyl-4-phenylbutyl)aminoethyl]-salicylamide.

5-[1-hydroxy-2-(1-methyl-3,3-diphenylpropyl)aminoethyl]salicylamide.

5-[2-(1,1-dimethyl-3-phenylpropyl)-amino-1-hydroxyethyl]salicylamide.

5-[1-hydroxy-2-(1-methyl-3-p-tolyl-propyl)aminoethyl]salicylamide hydrochloride.

5-{1-hydroxy-2-[3-(3,4-dimethoxypropyl)-1-methylpropyl]aminoethyl}salicylamide hydrochloride.

The invention extends to the physiologically acceptable acid addition salts of the compounds of formula II, and these are in general preferred for administration. Preferred salts include the hydrochloride, sulphate, maleate, tartrate and citrate.

The compounds according to the invention may exist in isomeric form by virtue of the fact that they contain at least one asymmetric carbon atom. The invention includes all possible optically active forms and racemic mixtures of the compounds. The racemic mixtures may be resolved by conventional methods, for example by salt formation with an optionally active acid, followed by fractional crystallization. The compounds which include an asymmetric centre in the group $R^1$ have two centres of asymmetry and can exist as four optical enantiomorphs. An example of the separation of a racemic mixture of such a compound into two racemic diastereoisomeric modifications is given hereinafter.

The 1-phenyl-2-aminoethanol derivatives of the invention may be prepared by a number of processes.

In one process, the compounds of the invention are prepared by reacting the ketones of general formula III with a halogen, preferably bromine, to form the haloketones of formula IV, followed by condensation with an amine $NHR^2R^3$, in which $R^2$ represents hydrogen, benzyl or the group $R^1$, and $R^3$ represents hydrogen or benzyl, to give the aminoketones of formula V.

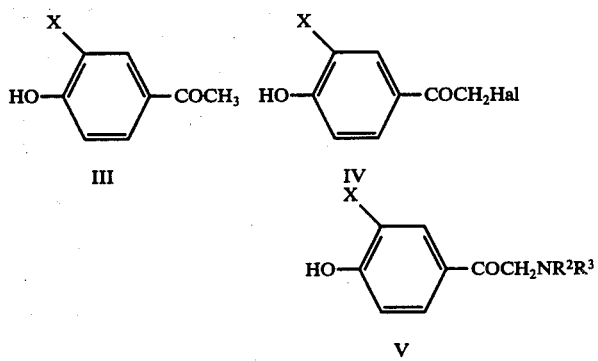

X represents the group —$CONH_2$, or a group convertible thereto.

The carbonyl group is then reduced to a CHOH group with a suitable reducing agent, for example a complex metal hydride such as sodium borohydride, or by catalytic hydrogenation, to give the 1-phenyl-2-aminoethanol derivatives of formula VI.

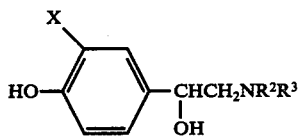

The compounds of the formula VI in which X is a —$CONH_2$ group, $R^2$ represents the radical $R^1$, and $R^3$ is a hydrogen atom are compounds of the invention. Other compounds of formula VI may be converted to compounds of the invention by the following procedures.

The group X is conveniently an alkoxycarbonyl radical of formula —$COOR^4$, where $R^4$ is a straight or branched chain alkyl radical containing from 1 to 6 carbon atoms. This group may be converted to a —$CONH_2$ group at any convenient stage in the synthesis of the compounds of formula II, by reaction with ammonia or an ammonia yielding compound.

The compounds in which $R^2$ and/or $R^3$ represent benzyl groups may be converted into the compounds in which $R^2$ and/or $R^3$ represent hydrogen atoms by catalytic hydrogenolysis.

The compounds in which $R^2$ and $R^3$ represent hydrogen atoms may be converted into the compounds in which $R^2$ is the radical $R^1$ by condensation with an appropriate aldehyde or ketone, followed by reduction of the azomethine so formed, with for example a complex metal hydride or hydrogen and a noble metal catalyst. For example, when the carbonyl compound used in this reaction is 4-phenyl-2-butanone, $CH_3COCH_2CH_2Ph$, the resulting $R^1$ radical is —CH(Me)$CH_2CH_2Ph$.

Alternatively, the compounds in which both $R^2$ and $R^3$ represent benzyl groups may be subjected to reductive alkylation with an appropriate carbonyl compound, to give the compounds in which $R^2$ is $R^1$, and $R^3$ is hydrogen, in one step.

It will of course be understood that the reactions used for converting the group —$COOR^4$ to a —$CONH_2$, for reducing the carbonyl group to the CHOH group, and for converting the group —$CH_2NR^2R^3$ to —$CH_2NHR^1$ may be carried out in any desired order at any convenient stage in the synthesis of the compounds of formula II.

In an alternative process for the production of the compounds according to the invention, a glyoxal of formula VII, in which X has the meaning given below, is used as the starting material. On reaction with an amine of formula $R^1NH_2$, the glyoxal yields an intermediate azomethine of formula VIII, which is then reduced, with for example, a complex metal hydride e.g. sodium borohydride, or hydrogen and a noble metal catalyst, followed if necessary by conversion of the group X to —$CONH_2$, to give a compound of formula II

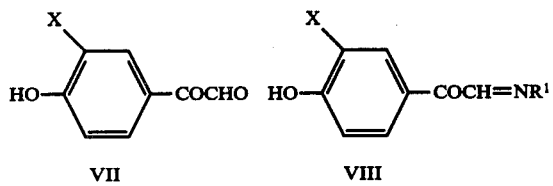

This method is described in application Ser. No. 699,263 referred to above the disclosure of which is herein incorporated by way of reference.

The phenolic hydroxy group of the starting materials and intermediate compounds may if desired be protected, e.g. as a benzyl ether or an acetate, during the synthesis. The protecting group is removed when required by hydrolysis or catalytic hydrogenolysis.

The compounds according to the invention may be formulated for use in human or veterinary medicine for therapeutic or prophylactic purposes. The invention therefore includes within its scope pharmaceutical compositions comprising as active ingredients compounds of general formula II or physiologically acceptable addition salts thereof. As stated preferred salts include the hydrochloride, sulphate, maleate, acetate, fumarate, lactate and citrate. Such compositions may be presented for use in a conventional manner with the aid of carriers or excipients and formulatory agents as required, and with or without supplementary medicinal agents. These compositions include, for instance, solid or liquid preparations for oral use, suppositories and injections. Oral administration is most convenient in the form of tablets which may be prepared according to conventional methods and may be coated if desired. Injections may be formulated with the aid of physiologically acceptable carriers and agents as solutions, suspensions, or as dry products for reconstitution before use. The doses of the active ingredient which may be used may vary within a wide range. Suitable doses are generally within the range of 5 mg to 1000 mg preferably 20 mg to 200 mg.

The following Examples illustrate the invention:

EXAMPLE 1

5-[1-Hydroxy-2-(1-methyl-3-phenylpropyl)aminoethyl]salicylamide hydrochloride

Method 1 a. 5-Bromoacetylsalicylamide (2.6 g), N-benzyl-N-(1-methyl-3-phenylpropyl)amine (4.8 g) and methyl ethyl ketone (50 ml were heated at reflux for 40 minutes. The solvent was removed and the residue was treated with benzene. The secondary amine hydrobromide was filtered off and discarded, and the filtrate was evaporated to dryness. The residue was treated with an excess of ethanolic hydrogen chloride when 5-[N-benzyl-N-(1-methyl-3-phenylpropyl)glycyl]salicylamide hydrochloride (1.15 g) crystallised out, m.p. 139°–141°.

b. 5-[N-benzyl-N-(1-methyl-3-phenylpropyl)glycl]-salicylamide hydrochloride (0.75 g), 10% mixture of PdO and PtO on carbon catalyst (0.1 g) and ethanol (20 ml) were shaken at room temperature and pressure with hydrogen until uptake ceased. The catalyst was filtered off and the filtrate evaporated to dryness. The residue was crystallised from ethanol to give 5-[1-hydroxy-2-(1-methyl-3-phenylpropyl)aminoethyl]salicylamide hydrochloride as a white solid (0.40 g), m.p. 188°.

Method 2

5-(N,N-dibenzylglycyl)salicylamide (2.25 kg), benzylacetone (990 g), 10% mixture of PdO and PtO on carbon (150 g), methanol (10 liters) and glacial acetic acid (378 ml) were stirred at 50° in an atmosphere of hydrogen until 586 liters of hydrogen had been absorbed. The catalyst was filtered off, and the filtrate was evaporated under reduced pressure to a viscous gum, which was dissolved in ethanol (4 liters). Hydrogen chloride (216 g) in ethanol (2.16 liters) was added, followed by ether (5 liters). The hydrochloride was filtered off and dried.

The crude solid (1.79 kg) was recrystallised from a mixture of ethanol (10 liters.) and ethyl acetate (15 liters) to give 5-[1-hydroxy-2-(1-methyl-3-phenylpropyl)aminoethyl]salicylamide hydrochloride as a white solid, (1.33 kg), m.p. 187°–9°.

EXAMPLE 2

5-[1-Hydroxy-2-(1-methyl-3-phenylpropyl)aminoethyl]salicylamide a. 5-(2-Amino-1-hydroxyethyl)salicylic acid methyl ester hydrochloride (5 g) in ammonium hydroxide (d. 0.880; 100 ml), was allowed to stand for 8 hours at room temperature. Removal of the solvent under reduced pressure left 5-(2-amino-1-hydroxyethyl)salicylamide hydrochloride, which crystallised from methanol-ethyl accetate as white needles (3.5 g), m.p. > 360°.

b. The amine hydrochloride from the previous experiment (2.3 g), in methanol, was neutralised with a solution of sodium hydroxide (0.4 g) in methanol (10 g). The mixture was concentrated and refluxed for 1 hour with 4-phenyl-2-butanone (1.5 g) in ethanol (100 ml), cooled and reduced by hydrogen at room temperature and pressure, in the presence of a 10% platinum — charcoal catalyst (1.0 g).

On completion of the reduction, the catalyst and solvent were removed to leave an oil, which was extracted with ethyl acetate, and filtered to remove inorganic material. Evaporation of the solution gave a residue which was triturated with ether to yield 5-[1-hydroxy-2-(1-methyl-3-phenylpropyl)aminoethyl]-salicylamide as a white solid, m.p. 136°–139°. Crystallization from ethyl acetate-cyclohexanone raised the melting point to 141°–143°.

The compounds shown in Table I were prepared by reacting 5-(2-amino-1-hydroxyethyl)salicylamide hydrochloride with the appropriate carbonyl compound, using the general method of Example 2(b).

TABLE I

H₂NOC—[phenyl ring with HO— and —CHCH₂NHR with OH]

| Example No. | Name of Compound | R | Melting Point °C | Yield % |
|---|---|---|---|---|
| 3 | 5-[1-hydroxy-2-(p-methoxy-α-methylphenethyl) aminoethyl]salicylamide | —CH(CH₃)—CH₂—C₆H₄—OMe | 155 | 73.05 |
| 4 | 5-[1-hydroxy-2-(2-p-methoxyphenoxy-1-methylethyl)aminoethyl]salicylamide | —CH(CH₃)—CH₂—O—C₆H₄—OMe | 113 | 42 |
| 5 | 5-[1-hydroxy-2-(3-p-methoxyphenyl-1-methylpropyl)aminoethyl]salicylamide | —CH(CH₃)—CH₂—CH₂—C₆H₄—OMe | 151 | 63 |
| 6 | 5-[1-hydroxy-2-(3-phenylpropyl)aminoethyl]salicylamide hydrochloride | —CH₂—CH₂—CH₂—C₆H₅ | 200 | 28 |

TABLE I-continued

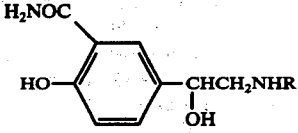

| Example No. | Name of Compound | R | Melting Point °C | Yield % |
|---|---|---|---|---|
| 7 | 5-[1-hydroxy-2-(2-o-methoxyphenoxy-1-methyl-ethyl)aminoethyl]salicylamide | 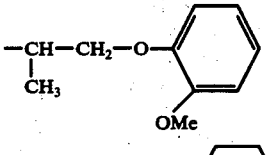 | 127 | 53 |
| 8 | 5-[1-hydroxy-2-(3-p-hydroxyphenyl-1-methyl-propyl)aminoethyl]salicylamide hydrochloride | 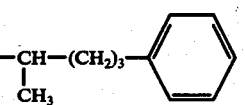 | 170 | 47 |
| 9 | 5-[1-hydroxy-2-(1-methyl-4-phenylbutyl)-amino]ethylsalicylamide | —CH—(CH₂)₃—⌬<br>\|<br>CH₃ | 151 | 42 |
| 10 | 5-[2-(1-methyl-3,3-diphenylpropyl)-amino-1-hydroxyethyl]salicylamide hydrochloride | —CH—CH₂CH Ph₂<br>\|<br>CH₃ | 177 | 50 |
| 11 | 5-[1-hydroxy-2-(1-methyl-3-p-tolyl-propyl)aminoethyl]salicylamide hydrochloride | 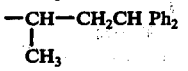 | 220 (as hydrochloride) 233 | 20 |
| 12 | 5-{1-hydroxy-2-[3-(3,4-dimethoxyphenyl)-1-methylpropyl]aminoethyl}salicylamide hydrochloride |  | 115–118 | 40 |

EXAMPLE 13

5-[1-Hydroxy-2-(1,1-dimethyl-3-phenylpropyl)aminoethyl]salicylamide

A solution of 5-glyoxyloysalicylic acid methyl ester hydrate (1.58 g) and 1,1-dimethyl-3-phenylpropylamine (1.2 g) in methanol (20 ml) was reflaxed for 30 minutes and then evaporated. The residue was dissolved in ethanol (50 ml) and was hydrogenated at room temperature and pressure in the presence of 10% platinum-charcoal (0.5 g). Addition of methanol (50 ml), glacial acetic acid (0.45 ml) and more catalyst facilitated the reduction.

When hydrogenation was complete, catalyst and solvent were removed, and the residual oil was neutralised with sodium bicarbonate and extracted into ethyl acetate. The organic layer was shaken with concentrated hydrochloric acid, washed with water, dried over magnesium sulphate and evaporated. The yellow oily residue crystallised from ethyl acetate-ether to give 5-[1-hydroxy-2(1,1-dimethyl-3-phenyl-propyl)aminoethyl]salicylic acid methyl ester hydrochloride, m.p. 170° (40% yield).

A solution of the above hydrochloride (0.6 g) in methanol (10 ml) and ammonium hydroxide (d. 0.880; 10 ml) was allowed to stand at room temperature for 48 hours. On evaporation, a residue was obtained which was neutralised with sodium bicarbonate solution and extracted with ethyl acetate. When dried and evaporated, the solution gave the amide as a white solid, m.p. 154° (63% yield).

A similar reductive alkylation using 5-glyoxyloyl salicylamide hydrate and 1,1-dimethyl-3-phenyl-propylamine yielded the same compound.

EXAMPLE 14

The separation of 5-[1-hydroxy-2-(1-methyl-5-phenylpropyl) aminoethyl]salicylamide hydrochloride into the two racemic modifications. Isomer 1 and Isomer 2 a. Isomer 1

5-[1-Hydroxy-2-(1-methyl-3-phenylpropyl)aminoethyl]salicylamide (3.3g) from Example 2(b) above and benzoic acid (1.2 g) were mixed and dissolved in hot ethanol (7 ml). Ether (20 ml) was added and the solution was filtered. A further quantity of ether (80) was then added, and the solution was allowed to stand at 0° for 17 hours. The fine white solid was filtered off and dried at 25° in vacuo to give the benzoate (2.0 g), m.p. 83°–85°. The filtrate was reserved for the preparation of Isomer 2.

The benzoate was dissolved in ethanol (4 ml), ether (50 ml) was added, and the solution was allowed to stand at 0° for 17 hours. The solid was filtered off and dried at 25° in vacuo to give the benzoate of Isomer 1 (1.5 g) m.p. 90°–92°.

A solution of the above compound in ethanol was treated with a slight excess of ethanolic hydrogen chloride to give the hydrochloride of Isomer 1, (1 g), m.p. 220°.

b. Isomer 2

The filtrate from the preparation of the crude benzoate of Isomer 1 was evaporated, and the residue was crysallised from ethyl acetate to give a white crystalline solid (2.0 g), m.p. 135.6°. Recrystallisation from ethyl acetate gave the benzoate of Isomer 2, (1.5 g) m.p. 141°–142°.

A solution of the above compound in ethanol was treated with a slight excess of ethanolic hydrogen chloride, followed by an equal volume of ether, to give the hydrochloride of Isomer 2, (1.0 g), m.p. 174°.

The following Examples are of pharmaceutical compositions according to the invention. The references to active ingredient in these Examples means a compound according to the invention and in particular one of the specific compounds the preparation of which is described in the foregoing Examples.

EXAMPLE 15

Capsules

To prepare 10,000 capsules each containing 20 mg. active ingredient

Mix together 200 g. powdered active ingredient with a sufficient quantity of microcrystalline cellulose B.P.C. and fill into No. 3 hard gelatin capsules so that each capsule contains about 120 mg. of the mixture.

Capsules may similarly be prepared each containing 50 mg. of active ingredient.

EXAMPLE 16

Tablets

To prepare 5,000 tablets each containing 100 mg. active ingredient

Mix together 500 g. active ingredient, 490 g. microcrystalline cellulose B.P.C., 5 g. magnesium stearate and 5 g. stearic acid B.P. Compress the powders on a suitable tableting press to produce tablets each ¼ inch in diameter and weighing about 200 mg.

To prepare 5,000 tablets each containing 200 mg. active ingredient

Mix together 1,000 g. active ingredient, 500 g. lactose and 175 g. maize starch and sufficient of a 2% aqueous solution of sodium hydroxyethyl cellulose to produce a damp cohesive mass. Pass the damp mass through a No. 14 mesh B.S.S. sieve and dry in a fluidised bed dryer at 60° C. Pass the dried granules through a No. 22 B.S.S. sieve and mix with 60 g. dried maize starch and 15 g. magnesium stearate. Compress the lubricated granules on suitable tableting press using ⅜ inch deep concave punches to produce tablets each weighing about 350 mg.

These tablets may be film coated with suitable film forming materials such as methyl cellulose, hydroxypropylmethyl cellulose or ethyl cellulose or mixtures of these materials using standard techniques.

The tablets may also be sugar coated by the standard sugar coating techniques.

EXAMPLE 17

Injection

To prepare an injection containing 10 mg. active ingredient per ml.

Dissolve 10 g. active ingredient and 7.5 g. sodium chloride in 950 ml. water for injection. When solution is complete make up to 1 liter with more water for injection. Subdivide the solution into suitable size ampoules (1 ml., 5 ml., or 10 ml.) seal and sterilize by heating in an autoclave.

What is claimed is:

1. A pharmaceutical composition for the treatment of hypertension, comprising as active ingredient, an effective amount of 5-[1-hydroxy-2-(1-methyl-3-phenylpropyl)aminoethyl]salicylamide or a physiologically acceptable acid addition salt thereof in association with a non-toxic pharmaceutically acceptable carrier.

2. A composition as claimed in claim 1 in which said active ingredient is 5-[1-hydroxy-2-(1-methyl-3-phenylpropyl) aminoethyl] salicylamide.

3. A composition as claimed in claim 1 in which said active ingredient is 5-[1-hydroxy-2-(1-methyl-3-phenylpropyl) aminoethyl) salicylamide hydrochloride.

4. A composition as claimed in claim 1 in dosage unit form containing from 5 mg to 1000 mg of said active ingredient.

5. A composition as claimed in claim 4 containing from 20 mg to 200 mg of said active ingredient.

6. A composition as claimed in claim 5 in the form of a tablet.

7. A method of treating a human patient suffering from hypertension by blocking both $\alpha$- and $\beta$-adrenergic receptors in the patient, characterized in that there is administered orally, by suppository or by injection, an effective amount of a compound having both $\alpha$- and $\beta$-blocking activity, which compound is 5-[1-hydroxy-2-(1-methyl-3-phenylpropyl)aminoethyl] salicylamide or a physiologically acceptable acid addition salt thereof.

8. A method as claimed in claim 7 in which said compound is administered orally.

9. A method as claimed in claim 8 in which said compound is administered in tablet form.

10. A method as claimed in claim 9 in which each tablet contains from 20 mg to 200 mg of said compound.

* * * * *